United States Patent [19]

Hammond et al.

[11] Patent Number: 5,747,839

[45] Date of Patent: May 5, 1998

[54] CHEMICAL SENSING TRENCH FIELD EFFECT TRANSISTOR

[75] Inventors: Jonathan H. Hammond, Scottsdale; Young Sir Chung, Gilbert, both of Ariz.

[73] Assignee: Motorola, Inc., Schaumburg, Ill.

[21] Appl. No.: 720,513

[22] Filed: Sep. 30, 1996

[51] Int. Cl.[6] .................................................. H01L 23/58
[52] U.S. Cl. ........................ 257/253; 257/252; 257/401; 257/414
[58] Field of Search .................................. 257/252, 253, 257/401, 414

[56] References Cited

U.S. PATENT DOCUMENTS

| | | | |
|---|---|---|---|
| 4,764,797 | 8/1988 | Shaw et al. | 257/253 |
| 4,874,499 | 10/1989 | Smith et al. | 204/403 |
| 4,961,833 | 10/1990 | Sakai et al. | 204/403 |
| 5,414,284 | 5/1995 | Baxter et al. | 257/253 |
| 5,576,563 | 11/1996 | Chung | 257/253 |

*Primary Examiner*—Mahshid D. Saadat
*Assistant Examiner*—Allan R. Wilson
*Attorney, Agent, or Firm*—Daniel R. Collopy

[57] ABSTRACT

A field effect transistor (10) for chemical sensing by measuring a change in a surface potential of a gate electrode (48) due to exposure to a fluid has a semiconductor substrate (12) with a trench (18, 20). The trench has a first sidewall (30) and a second sidewall (32) disposed opposite the first sidewall to provide a fluid gap (50) for the fluid to be sensed. The gate electrode is disposed overlying the first sidewall of the trench, and a source region (54) and a drain region (56) are disposed in the second sidewall of the trench. A channel region (52) is disposed between the source and drain regions, and the gate electrode is disposed opposite the first channel region across the fluid gap. A heater (26) for regulating the temperature of the gate electrode is disposed in the first sidewall of the trench.

6 Claims, 3 Drawing Sheets

CHEMICAL SENSING TRENCH FIELD EFFECT TRANSISTOR

BACKGROUND OF THE INVENTION

The present invention relates, in general, to semiconductor devices and, more particularly, to a field effect transistor for measuring a change in surface potential of the transistor's gate electrode due to exposure to a chemical as used in, for example, a chemical sensor.

Field effect transistors have been previously used in some cases as chemical sensors for measuring the concentration of a chemical in a fluid. One such prior sensor uses a gate electrode that is horizontally suspended over the channel region so as to provide a gap in which fluid may enter and contact an exposed surface of the gate electrode. A chemical in the fluid, to which the gate electrode is particularly sensitive, is adsorbed onto the exposed surface and changes the surface potential of the gate electrode. The drain current of the transistor changes in response to this surface potential change. Thus, if a constant gate voltage source is applied to the gate electrode during sensing, the change in drain current can be correlated to the concentration of the chemical in the fluid.

It has been found that the surface chemical reactions of this prior sensor, which include adsorption/desorption reactions of the chemical to be sensed onto and off of the exposed gate electrode surface, are very sensitive to temperature, so it is desirable that the temperature of the gate electrode be more directly regulated to optimize the output of the sensor. Also, it has been found to be desirable that this temperature be elevated above the ambient temperature to provide improved performance for the sensor. However, prior chemical sensors do not provide an integrated heating element for direct temperature control of the gate electrode. Instead, an external heater is required to heat the entire sensor assembly, rather than the gate electrode directly. Such an external heater is inconvenient to provide in a final, fully-manufactured chemical sensor assembly and increases the manufacturing cost thereof. Also, an external heater requires significant power consumption during operation.

In addition to the above, it is important that the gap size of the sensing transistor be readily controllable during manufacture so that the operating characteristics of the transistor are consistent over a large number of manufactured sensors. Also, it is important that the gap structure be stable under thermal loads, and the gap structure should be mechanically robust to improve reliability along with ease of handling and packaging.

Further, the mechanical structure of the transistor should permit ready diffusion of the fluid to be sensed into and out of the gap of the transistor. This ready diffusion is important to provide a faster response time of the sensor to chemical changes in the fluid. These changes cannot be fully sensed until the species corresponding to the chemical change diffuses through the gap of the transistor structure to contact the gate electrode of the sensor. Prior sensor structures do not provide a readily controllable gap size and such ready diffusion into the gap. Further, prior sensor structures need to be more compatible for integration into standard device process flows for devices for control circuitry incorporated on the same chip as the sensor.

Accordingly, there is a need for a chemical sensing field effect transistor that provides an integrated heater and a fluid gap in a transistor structure that permits improved control of the gap size, improved diffusion of a fluid into the gap, and improved compatibility with other standard device process flows.

DETAILED DESCRIPTION OF THE DRAWINGS

The present invention generally provides a chemical sensing semiconductor device having a trench and provides in one specific embodiment a trench field effect transistor for measuring a change in the surface potential of the transistor's gate electrode due to exposure of the electrode to a fluid. As used herein, the term "fluid" includes both gaseous and liquid fluids. Typically, the gate electrode is a metal onto which chemicals to be sensed adsorb. The adsorption causes a change in the surface potential of the metal that then modulates the conductivity of the channel region of the transistor. The gate electrode is disposed opposite the channel region across a gap containing the fluid to be sensed. By changing the material used for the gate electrode, the sensitivity of the transistor can be tailored to any of a broad spectrum of different chemicals at varying ranges of concentration.

Figure 1:
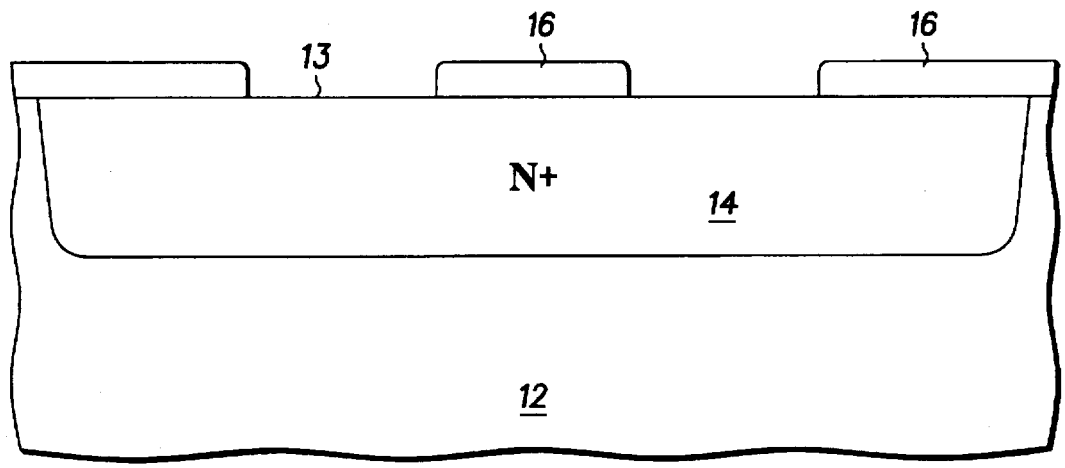
FIGS. 1–5 are enlarged cross-sectional views illustrating sequential steps in the manufacture of a chemical sensing field effect transistor according to the present invention.

FIGS. 1–5 are cross-sectional views illustrating sequential steps, for one specific embodiment, of the manufacture of a chemical sensing field effect transistor 10 according to the present invention. As will become apparent later, transistor 10 includes a plurality of devices connected in parallel. It is should be noted that FIGS. 1–5 are not drawn to scale and are exaggerated for purposes of illustration. FIG. 1 illustrates a semiconductor substrate 12 such as, for example, a P- silicon wafer. A doped region 14 of a conductivity type different from substrate 12 has been formed in substrate 12 by, for example, a high dose N+ implant of arsenic or phosphorous of about $1E15-1E16/cm^2$. This implant has been thermally driven in to a depth of, for example, about 0.5 to 10 microns from a top surface 13 of substrate 12. The depth of doped region 14, as will be seen later, corresponds to the channel width of each individual device to be formed in transistor 10.

A hard mask 16 has been formed and patterned on top surface 13 of substrate 12. Hard mask 16 is, for example, an oxide layer formed by plasma enhanced chemical vapor deposition (PECVD). Openings are formed in hard mask 16 by a conventional pattern and etch process and correspond to the position of trenches to be formed later in substrate 12.

Figure 2:
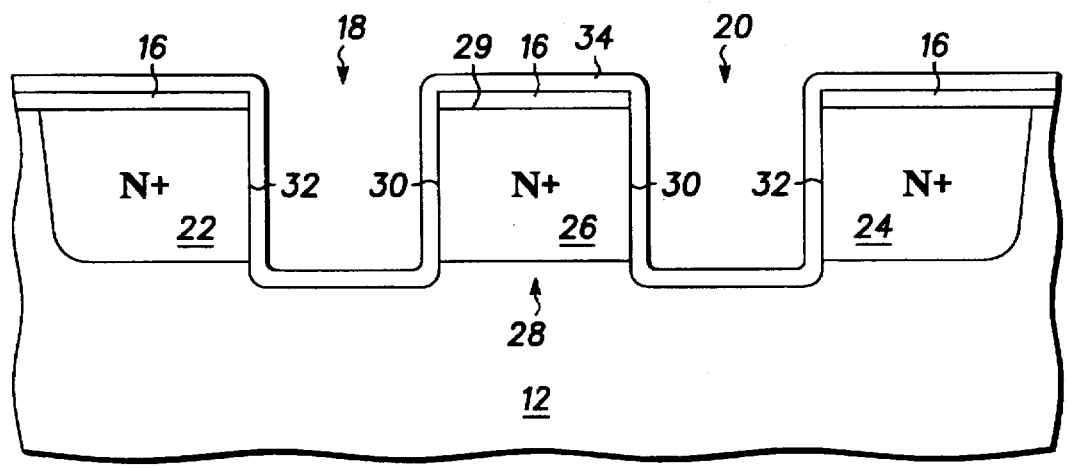

FIG. 2 illustrates substrate 12 after trenches 18 and 20 have been formed therein using a conventional anisotropic trench etching technique. For example, trenches 18 and 20 can be etched using a reactive ion etch in a standard chlorine or fluorine chemistry. The width of each trench has a minimum dimension of, for example, about 0.05 to 20 microns. Trenches 18 and 20 extend to a depth past the lower boundary of doped region 14 (see FIG. 1) so as to divide doped region 14 into portions corresponding to a drain 22, a source 24 and a heater 26. As will be discussed in more detail later, in a preferred embodiment drain 22, source 24, and heater 26 will have the same dopant concentration since they are formed in a single implant step from common doped regions 14. Alternatively, heater 26 may have a higher dopant concentration by the use of an additional, separate implanting step for the region of substrate 12 corresponding to heater 26.

It should be noted that hard mask 16 is somewhat reduced in thickness from the etching of trenches 18 and 20. Also, a ridge 28 having a top surface 29 is disposed between trenches 18 and 20 and corresponds to a continuous doped region that provides heater 26 (see FIG. 6).

Following the etching of trenches 18 and 20, a sidewall oxide layer 34 is formed, for example, using a PECVD oxide. Sidewall oxide layer 34 protects ridge sidewall 30 and outer sidewall 32 of each trench during subsequent etching steps.

One advantage of the present invention is that the width of each trench is determined by a photolithography patterning step rather than by the use of sacrificial layers or stand-off structures. This provides easier and more uniform control of each trenches width from one sensor chip to another. Further, as shown later, the trench width largely determines the size of the gap into which fluid enters for sensing (see fluid gap 50 of FIG. 5).

Figure 3:
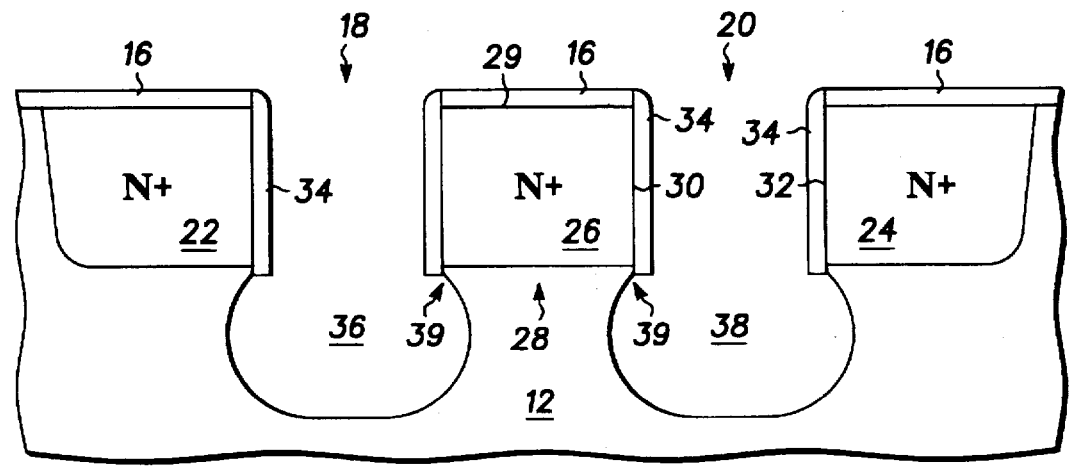

FIG. 3 illustrates the additional etching of trenches 18 and 20. First, in order to perform this additional etching, the portions of sidewall oxide layer 34 on the bottoms of each trench are removed using, for example, a conventional dry anisotropic oxide etch. For example, $CF_4$ at a low pressure can be used. It should be noted that this etching step also substantially removes the top portions of sidewall oxide layer 34 overlying hard mask 16.

After removing these bottom portions of layer 34, a cavity 36 and a cavity 38 are formed by a two-step etching process. First, an anisotropic etch using similar chemistry as the prior anisotropic etch above is used to extend the depth of each trench. The depth to which each trench is extended is determined in part by the desire to electrically isolate a gate electrode 48 (see FIG. 5), which will be formed later over ridge 28, from the source and drain regions of the final sensor. For example, the depth may be extended by up to about 50 percent.

Second, an isotropic etch is performed using, for example, $SF_6$ to provide an undercut 39 in each trench. As will be seen later, after gate electrode 48 (see FIG. 5) is later formed over ridge 28, undercut 39 will assist in electrically isolating any stray gate electrode formation material that might remain on outer sidewall 32 overlying source or drain 22 or 24. Undercut 39 widens each cavity by, for example, about an additional 4–6 microns from the vertical sidewalls of each trench (i.e. the cavity width is greater than the upper trench width by about 4–6 microns). Undercut 39 in each of cavities 36 and 38 makes the manufacturing process more robust and facilitates later processing associated with the formation of the gate electrode by isolating the gate electrode from any stray gate electrode material in this way. Some of the factors that affect the degree of undercut 39 needed include the gate electrode thickness, the thickness of the later-formed gate oxide layer 40 (see FIG. 5), the size of fluid gap 50 (see FIG. 5), and the depth of each trench from the wafer surface to the cavity bottom. Following the formation of cavities 36 and 38, all remaining portions of sidewall oxide layer 34 and hard mask 16 are removed, for example, using a wet etch of HF.

Figure 4:
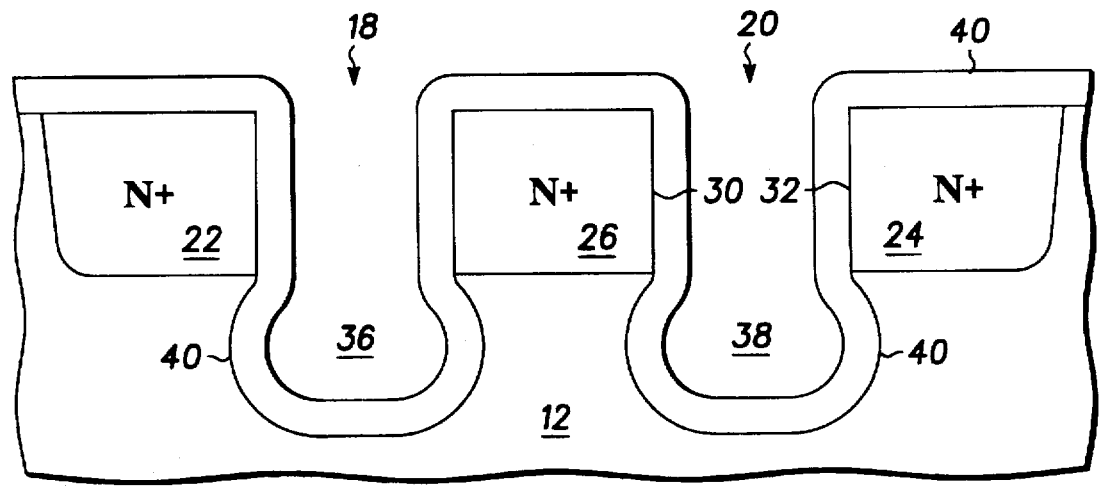

In FIG. 4, gate oxide layer 40 has been formed overlying drain 22, source 24, and heater 26 by, for example, thermally growing a silicon oxide layer to a thickness of about 400–5,000 angstroms. This is done in preparation for gate electrode 48.

Figure 5:
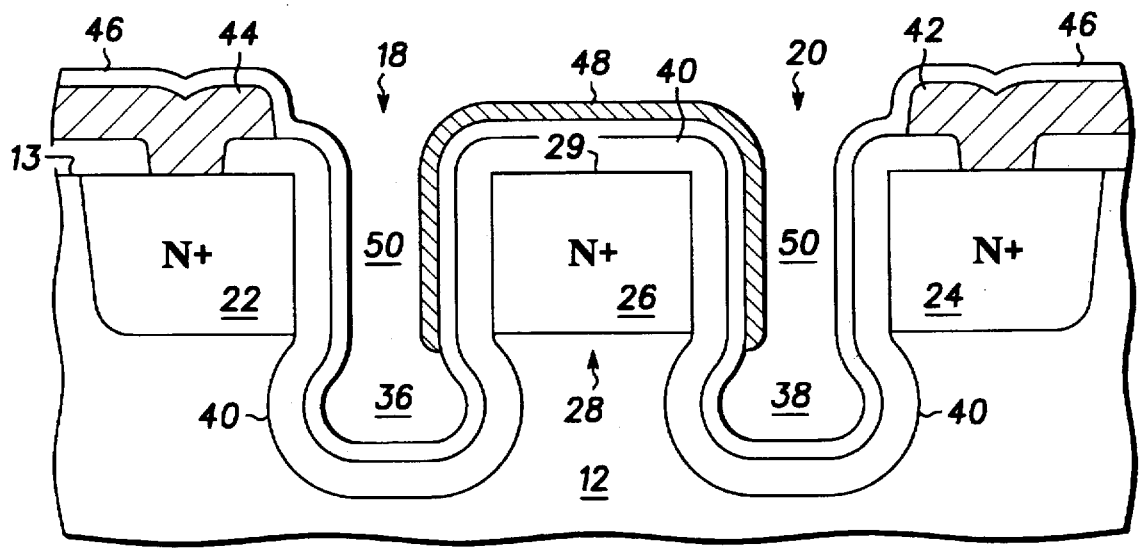

Now, referring to FIG. 5, source and drain contacts are opened and a first metal layer is formed using conventional techniques to provide a source electrode 42 and a drain electrode 44. These electrodes are formed, for example, using an aluminum alloy. It is preferable that the patterning of the first metal layer be done using a wet etch, but a dry etch is also acceptable. Next, a passivation layer 46 is formed overlying gate oxide layer 40 and overlying source and drain electrodes 42 and 44. Passivation layer 46 is, for example, a conformal silicon nitride layer formed by chemical vapor deposition to a thickness of about 1,500–7,000 angstroms. Also, although not illustrated in the figures, contact openings are formed to heater 26 on each of its ends (see FIG. 6 for a top view of heater 26).

The final processing step illustrated in FIG. 5 is the formation of gate electrode 48 which provides an adsorption layer for chemical adsorption from a fluid present in fluid gap 50. Gate electrode 48 is a continuous layer formed overlying top surface 29 of ridge 28 and is generally conformal to the topography of underlying passivation layer 46. The material used to form gate electrode 48 is selected depending on the particular chemical sensing application desired. For example, gate electrode 48 may be formed of a metal such as platinum, palladium, or alloys thereof. Fluid gap 50 permits fluid to contact gate electrode 48.

In the case of a metal gate electrode, gate electrode 48 can be formed by sputtering the metal into trenches 18 and 20 and over top surface 29. Next, the sputtered metal is patterned using a conventional thick photoresist and patterning chemistry. The thickness of gate electrode 48 will vary depending on the particular material selected and the sensing application, but typically this thickness varies between about 50–7,000 angstroms. Although sputtering is described here, it should also be appreciated that gate electrode 48 can also be deposited by other conventional processes including chemical vapor deposition.

Figure 6:
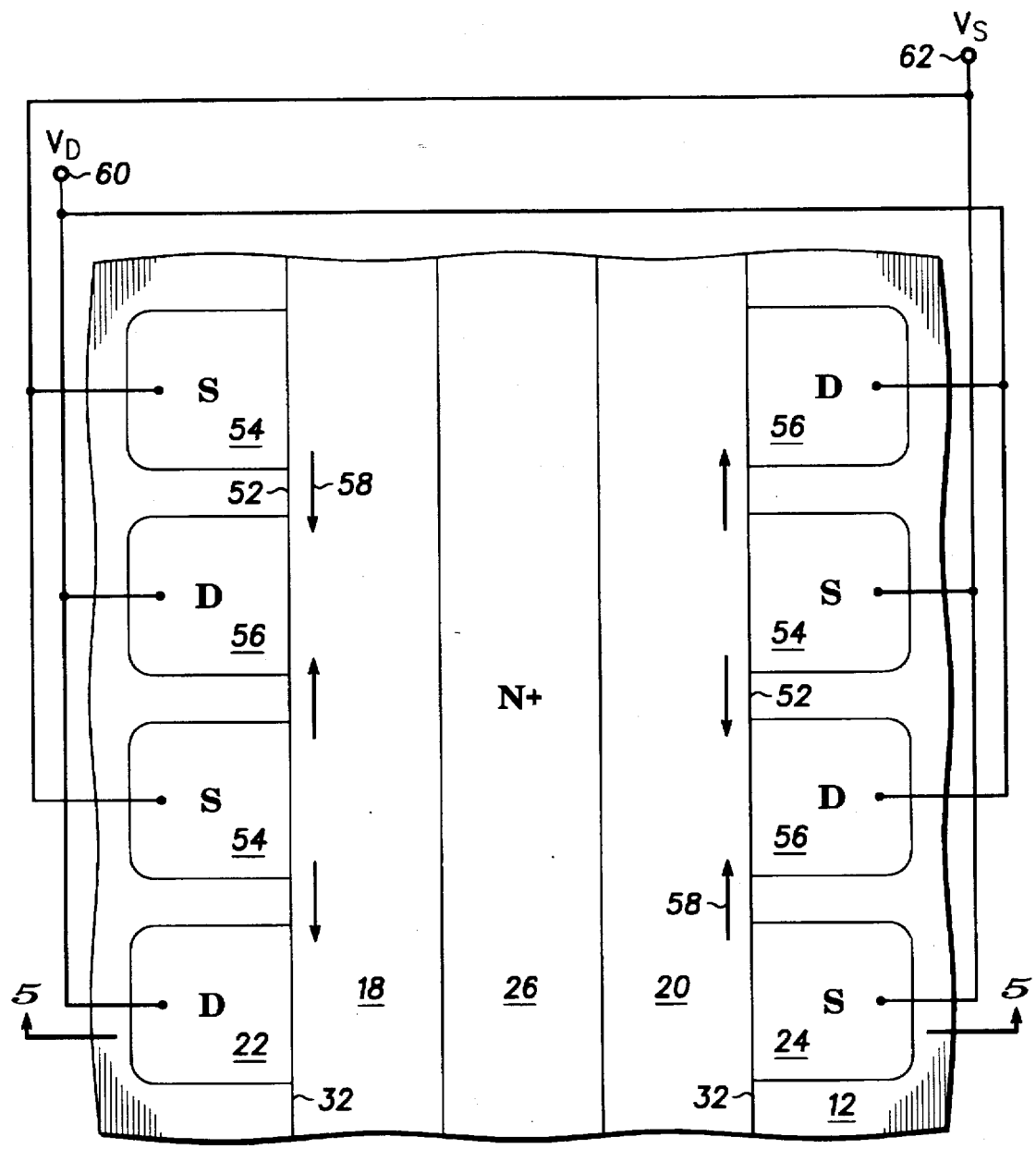
FIG. 6 is a top schematic view of the chemical sensing field effect transistor of FIG. 5

FIG. 6 is a top schematic view of transistor 10. It should be noted that for purposes of illustration FIG. 6 does not show gate electrode 48, passivation layer 46, source and drain electrodes 42 and 44, or gate oxide layer 40. In addition to drain 22 and source 24, transistor 10 in this illustrated embodiment includes a plurality of sources 54 and drains 56 connected in parallel. A plurality of channel regions 52 are each disposed on outer sidewalls 32 of trenches 18 and 20. Each channel region 52 carries a current 58 that flows laterally along outer sidewall 32. It should be noted that this current does not flow from a source on one side of ridge 28 to a drain on the opposite side of ridge 28 by flowing underneath ridge 28.

Chemical sensing field effect transistor 10 has fluid gap 50 (see FIG. 5) between gate electrode 48 and the source and drain regions of transistors 10, which include drain 22 and source 24. In operation, a fluid enters fluid gap 50 and is adsorbed onto gate electrode 48. The adsorption of chemicals in the fluid onto gate electrode 48 changes the surface potential of the electrode and in turn modulates the conductivity of the corresponding channel region 52 (see FIG. 6) across fluid gap 50 on the opposite side of the respective trench. Another example of a chemical field effect transistor that uses chemical sensitivity of a gate electrode to chemical exposure is described in commonly-assigned U.S. application Ser. No. 08/427,389, filed on Apr. 24, 1995, by Young S. Chung and titled "CHEMICAL PROBE FIELD EFFECT TRANSISTOR FOR MEASURING THE SURFACE POTENTIAL OF A GATE ELECTRODE IN RESPONSE TO CHEMICAL EXPOSURE," which is hereby incorporated by reference in full. It should be appreciated that transistor 10 according to the present invention provides fluid gap 50 in a trench 18 or 20 that more readily permits diffusion of fluid into and out of the trench so that the response time of transistor 10 to changes in chemical concentrations is much greater compared to prior types of chemical sensing transistor structures.

The plurality of devices of transistor 10 are connected in parallel such that a common drain voltage bias is applied to each drain by a terminal 60, and a common source voltage bias is applied to each source by a terminal 62. Gate electrode 48 will be biased by a contact (not shown) on one of its ends to maintain the bias current necessary to achieve a useful signal-to-noise ratio from transistor 10. Heater 26 is used to control the temperature of gate electrode 48 and thereby regulate the absorption/desorption rate of chemicals in fluid gap 50 onto and from gate electrode 48. Heater 26 will be biased by contacts (not shown) on both of its ends to heat gate electrode 48 to a temperature optimal for these adsorption/desorption reactions at the gate electrode's surface. Also, heater 26 is electrically controllable independently of gate electrode 48. Transistor 10 is preferably operated in a depletion mode, having conducting channel regions 52 in the presence of little or no bias voltage on gate electrode 48. The channel length for each device is variable depending upon the particular application, but typically varies between about 0.05 to 20 microns. The overall length of each trench 18 or 20 depends on the particular device parameters, but can range for example between about 100 microns to 10 millimeters. The operating temperature range for transistor 10 also depends on the application, but a typical temperature range is from about 100°–550° K. Further, it is not necessary that two trenches be used. Instead, a single trench or multiple trenches having many different arbitrary geometrical configurations can be used.

As mentioned previously, the channel width of each device substantially corresponds to the depth of the corresponding doped region 14 (see FIG. 1) into substrate 12. With the devices of transistor 10 connected in such a parallel configuration, the overall width/length (W/L) ratio for transistor 10 is given by W(n−1)/L, where W is the depth of doped region 14, n is the number of source and drain regions, and L is the channel length. As the length of each trench is increased, additional source/drain diffusions can be added so that a longer trench will provide a higher overall W/L ratio.

Chemical sensing is accomplished by measuring changes in the overall drain current of transistor 10, for example, at terminal 60. Because the drain current is directly proportional to the overall W/L of transistor 10, the length of each trench is selected to provide a drain current of a sufficient magnitude for measurement by the control electronics on the sensor.

As discussed previously, doped region 14 of FIG. 1 is used to provide drain 22 and source 24 after the etching of trenches 18 and 20 (see FIG. 5). As is illustrated in FIG. 6, transistor 10 has a plurality of sources 54 and drains 56. Each source and drain pair in this specific embodiment is disposed symmetrically across heater 26 and corresponds to a doped region formed earlier in the processing sequence such as doped region 14 of FIG. 1. In a preferred approach, sources and drains 54 and 56 along with heater 26 are formed by a single implant mask pattern including several adjacent doped regions 14 connected by a spine-like portion of the implant pattern corresponding to heater 26.

By now it should be appreciated that there has been provided a novel chemical sensing transistor that integrates a heater into a device structure using a trench to define the size of the fluid gap. This trench structure provides improved diffusion of fluid into and out of the gap leading to improved response time of the sensing transistor to changes in chemical concentration. Further, the trench structure of transistor 10 makes it more manufacturable than prior sensors due to the improved precision and accuracy associated with forming fluid gap 50. Transistor 10 is also more mechanically stable under thermal stresses induced by heater 26 and the environment in which the final sensor package is used. This improved mechanical structure improves long-term device reliability, and ease of handling and testing through qualification and delivery to an end user.

The chemical sensing transistor of the present invention is useful in a wide number of applications including the sensing of gaseous hydrides, oxygenated organic vapors, sulfur compounds, and other gaseous or liquid species that cause a reversible work function change of the gate electrode.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

We claim:

1. A field effect transistor for measuring a change in a surface potential of a gate electrode due to exposure to a fluid, said field effect transistor comprising:

a semiconductor substrate having a first trench and a second trench disposed on opposite sides of a ridge protruding upward between said first trench and said second trench, wherein said first trench has a first fluid gap, said second trench has a second fluid gap, and each of said first trench and said second trench has a ridge sidewall disposed on said ridge and an outer sidewall disposed opposite said ridge sidewall;

a first source region and a first drain region disposed on said outer sidewall of said first trench; and a second source region and a second drain region disposed on said outer sidewall of said second trench, wherein said gate electrode has a first portion disposed overlying said ridge sidewall of said first trench and a second portion overlying said ridge sidewall of said second trench.

2. The field effect transistor of claim 1 wherein said gate electrode is a continuous layer including said first port ion and said second portion and further overlying a top surface of said ridge.

3. The field effect transistor of claim 2 further comprising a heater disposed in said ridge.

4. The field effect transistor of claim 3 wherein said first drain region and said second source region are disposed in substantially symmetric positions across said ridge.

5. The field effect transistor of claim 1 wherein said semiconductor substrate further comprises a first cavity connected to and underlying said first trench and a second cavity connected to and underlying said second trench.

6. The field effect transistor of claim 5 wherein said first source region and said second source region are coupled to a common source voltage bias, and said first drain region and said second drain region are coupled to a common drain voltage bias.

* * * * *